(12) United States Patent
Wood (10) Patent No.: US 7,669,114 B2
(45) Date of Patent: *Feb. 23, 2010

(54) SOFTWARE ARCHITECTURE AND SYSTEM FOR PERFORMING VALIDATED CLINICAL STUDIES OF PHARMACEUTICAL RELATED PRODUCTS

(75) Inventor: Thomas Wood, Bridgewater, NJ (US)

(73) Assignee: Clynisys, Inc., Greenbrook, NJ (US)

( * ) Notice: Subject to any disclaimer, the term of this patent is extended or adjusted under 35 U.S.C. 154(b) by 1076 days.

This patent is subject to a terminal disclaimer.

(21) Appl. No.: 11/123,720

(22) Filed: May 6, 2005

(65) Prior Publication Data

US 2005/0210026 A1    Sep. 22, 2005

Related U.S. Application Data

(63) Continuation of application No. 10/264,919, filed on Oct. 4, 2002, now Pat. No. 6,925,599.

(51) Int. Cl.
*G06F 17/00* (2006.01)
*H04N 7/16* (2006.01)
*H04L 9/00* (2006.01)

(52) U.S. Cl. .................... 715/205; 715/229; 715/255; 715/234; 726/26; 713/179

(58) Field of Classification Search .................. 715/200, 715/221, 224, 225, 226, 229, 255, 256, 273, 715/700, 731, 736, 737, 738, 741, 742, 743, 715/760, 762; 705/3, 18, 50, 62, 64, 72, 705/76; 726/1, 2, 4, 26–30; 713/176, 177, 713/179, 180

See application file for complete search history.

(56) References Cited

U.S. PATENT DOCUMENTS

| | | | |
|---|---|---|---|
| 5,666,490 A | | 9/1997 | Gillings et al. |
| 5,671,282 A | * | 9/1997 | Wolff et al. .................. 713/179 |
| 5,734,883 A | * | 3/1998 | Umen et al. .................... 707/1 |
| 6,205,455 B1 | | 3/2001 | Umen et al. |
| 6,505,218 B2 | * | 1/2003 | Umen et al. ................. 715/236 |
| 6,854,086 B2 | * | 2/2005 | Umen et al. ................. 715/236 |
| 7,299,502 B2 | * | 11/2007 | Schmeling et al. ............ 726/29 |

FOREIGN PATENT DOCUMENTS

| | | | |
|---|---|---|---|
| EP | 0832462 B1 | * | 8/2002 |
| WO | WO 96/34348 | * | 10/1996 |

OTHER PUBLICATIONS

CDC Solutions: "Planning Your Transition to: Electronic Document Management Systems" Registration Form, Madison Hotel, Washington, DC, Mar. 23-25, 1994.*
P. Manell, "Pharmaceutical Document Management" (presentation slides), PharmaSoft AB, 12 pages, Feb. 12-15, 1995.*
CDC Solutions: ATLIS Consulting Group, Inc., "The CANDA Cook-Book; Preparing for Standards-Based CANDAs: A How-To-Guide", Jan. 1994, pp. 1-31.*

* cited by examiner

*Primary Examiner*—Laurie Ries
*Assistant Examiner*—Maikhanh Nguyen
(74) *Attorney, Agent, or Firm*—Kenneth R. Glynn, Esq; Dierdra M. Meagher, Esq (57) ABSTRACT

Software, and a master system with hardware and connections, for validated drug clinical studies includes: creating data collection documents with unique identifiers; having operators complete security identification verification before proceeding; having secured operators fill out and sign specified data collection documents; creating permanent records of the preceding; tracking by unique identifiers in a local system; uploading to a central system; independently reviewing filled out signed data collection documents to accept or require clarifications; keeping permanent read only records of all originally filled out and signed documents; making document clarification requests; reviewing each response; assigning new unique identifier links to each version of every revision; iteratively repeating the above until the documents are clean, and storing and tracking every version of every document in the central system; providing a monitor query and document entry history of all changes to all documents to create a secured audit trail.

20 Claims, 2 Drawing Sheets

SOFTWARE ARCHITECTURE AND SYSTEM FOR PERFORMING VALIDATED CLINICAL STUDIES OF PHARMACEUTICAL RELATED PRODUCTS

REFERENCE TO RELATED APPLICATION

This application is a continuation-in-part of U.S. application Ser. No. 10/264,919, filed on Oct. 4, 2002, now U.S. Pat. No. 6,925,599, and entitled "METHODOLOGY FOR PERFORMING VALIDATED CLINICAL STUDIES OF PHARMECEUTICAL RELATED PRODUCTS".

BACKGROUND OF THE INVENTION

1. Field of the Invention

The present invention relates to software architecture and systems for controlled education, sign-in, update, document creation, document editing, document trails, failsafe compilation and tracking and ultimate composition of content drug ("drug" as definable by FDA) documents and for organization, storage and retrieval thereof in one or more selected formats.

2. Information Disclosure Statement

The following patents represent clinical study documentation systems utilizing computers:

U.S. Pat. No. 6,205,455 describes a document production system which is provided for preparing documents and managing a database of information pertaining to investigational studies of medical products. The document production system includes a data management user interface for providing user access to the database and for retrieving information from the database as specified by selected document templates for placement into word processor-compatible documents. Additionally, the data management user interface is capable of updating information stored within the database in accordance with information specified within a previously-prepared document.

U.S. Pat. No. 5,666,490 describes an electronic document management system that converts documents into electronic images which can be sequentially routed to individual users in a network system. The network system includes at least two work nodes for processing the documents where one of the nodes is a data entry work node. The documents are subdivided into two or more subdivisions which are classified by subdivision type. The images are routed through the network system according to predefined routing schemes based on its subdivision type. The routing scheme for the documents includes at least one data entry node where data contained in the document is entered into a database. As the data is entered into the database, it is dynamically linked with its corresponding image which is also stored in the network.

Notwithstanding the prior art, the present invention is neither taught nor rendered obvious thereby.

SUMMARY OF THE INVENTION

The present invention involves software architecture and a system for performing validated clinical studies of drug-type products. The software provides for computerized steps that include: (a) creating a plurality of data collection documents that includes a plurality of diverse types of data collection documents, and a plurality of each diverse type of data collection document, wherein every individual data collection document is provided its own unique identifier; (b) providing operator security by having all operators and other data collectors and data handlers (The term "operators" and "operator" as used herein shall include the Principal Investigator, Investigators, Study Coordinators and other data collectors and data handlers.) complete identification verification before being permitted to proceed to add information into a local system utilizing the plurality of data collection documents; (c) having appropriate operators who have successfully completed operator security fill out and sign specified data collection documents for step (a) above, where required; (d) creating a permanent record of all filled out and signed data collection documents from step (c) and organizing and tracking the filled out and signed documents by their unique identifiers in the local system; (e) uploading said permanent record to a central system; (f) independently (e.g. by automatic review, comparison, etc.) reviewing the originally filled out and signed data collection documents to accept the documents as clean or to require clarifications, and keeping a permanent record of all originally filled out and signed documents, with no access for the operators to change or eliminate data; (g) as to the documents requiring clarifications, making clarification requests to the appropriate operator and procuring responses therefrom; (h) independently reviewing each response in the form of a revised document, assigning a unique identifier link to each version of every revised document and every subsequent version thereof, and repeating step (f) above iteratively until the documents are clean, and storing and tracking every version of every document in the central system; (i) procuring relevant external clinical documents where data were first recorded, the external clinical documents being selected from the group consisting of clinical notes, patient record form entries, laboratory results, and combinations thereof and, having the operators input the third party source clinical documents into the local system; (j) providing another level of independent data cleaning, source validation, reconciliation, identifications and storage through a monitor query system of communications between monitors and operators that includes the same procedures as set forth in steps (f), (g) and (h) above; (k) providing a document entry history to the local system and the central system of all changes to all documents within the local system to create an audit trail; (l) fully securing the audit trail as it is created so that it cannot ever be altered; and, (m) rendering the finished, clean, final version of each document, as fully secured document that may be read and may not be altered.

In some preferred embodiments, the present invention software includes a step or steps with a two part security clearance. This two part security clearance may include two different types of security clearance, at least one of which may be selected from the group consisting of password, voice recognition, signature recognition, retina recognition, fingerprint recognition, facial maps, biometric, or other available people identifiers and combinations thereof.

In preferred embodiments of the present invention software, the unique identifier includes a unique bar code. This bar code may be an encrypted bar code containing a plurality of document related information, two of the plurality of document information selected from the group consisting of title of study, site of study, operator, patient name, patient identification number, date, document version, interviewer, monitor, query number, and combinations thereof.

In some embodiments, the step (k) includes a data-by-data point of entry history to create an audit trail for every point of data entry having revisions. The local system is typically one of a plurality of local systems, and the central system is preferably an advanced computerized system with software to perform all of the steps stated above and below. Thus, for example, the audit trail may be a drop down window that is click accessed at each point of data entry having a history of at least one revision. Further, the filled out and signed data collection documents may be read by intelligent character recognition (ICR) for handwritten inputs and converted to digital representations for storage and retrieval. If an entry cannot be read by ICR, it will be treated as not clean and processed in accordance with steps (f), (g) and (h) above. The methodology step (m) preferably includes the use of digital signature technology to fully secure the documents wherein the documents cannot be altered without nullifying an attached digital signature. The fully secured documents may be locked by appending a private key generated digital signature thereto, and an operator's private key digital signature sign off creates said lock.

The present invention also includes a master system of various local computers that establish local systems, connected to at least one computer that establishes a central system for supervising, controlling, collecting and sending information and otherwise interacting with the local systems.

Many of the objectives stated above and in the Detailed Description below are achieved by the present invention software and system. The following represent additional objectives, advantages, and results achieved by the present invention software architecture and master system:

Users will not be permitted to proceed until properly passing security, reading all requirements/protocol, rules, revisions, etc. and will be forced to proceed as the central system requires, before being enabled to otherwise proceed.

A privacy masking feature allows capture of source documents (without Patient Identification) using, for example, identification numbers and initials so that transcribed CRFs can be checked against source documents remotely while online.

Source documents are linked to transcribe CRFs to eCRFs with related metadata in a manner that authenticates the user reviewing the linked documents, allows for visual validation and reconciliation of one related document to another and freezes in time the "signed off" package of documents.

Principle Investigators directly control the security authorizations and access rights to their local systems and database.

The present invention methodology flow allows for the acknowledgement of specific conditions or the independent measurement of activities never before measured. For example, current paper-based systems have CRFs filled out with the visit date noted. It would not be known if the visit date was correct or when the form was filled out. Our process would note the time the CRF was printed (from a system clock), when it was scanned, when it was further processed, etc. The series of independent system clock times coupled with the recorded visit date would help answer questions like: Was the CRF data recorded on the visit day? Was the SOP protocol of printing CRFs on the visit day followed? or How long after the visit did our process capture the data? Unlike any other system, the present invention not only tracks documents, but also tracks the absence of events/data on documents.

Forms may be printed that register when the workflow demand requires a higher level of security, authentication and document tracking.

Because work activities are defined with business rules, it is possible to track what is missing or what hasn't been done. An event, such as the authorization of a subinvestigator at a site, would trigger the necessity to acquire dozens of documents: resume, published articles, license to practice in state, etc. All these required documents would be missing until captured by the process. A second example could be that capturing a completed first visit would trigger the need to capture two lab reports from visit one in two days.

Another optional feature that may be included in preferred embodiments is taking a photo of the user at time of signing anything (only sponsor specified sign offs) would, as a practical matter, eliminate issues of authentication and non-repudiation.

The present invention process requires verifying local system clocks daily with the central database clock. Dates and times of clinical data and metadata are automatically screened by edit and logic checks.

True Remote Monitoring is enabled by having source documents linked metadata, the related transcribed, scanned CRF and ECRF all online and available to remote monitors in a completely secure, validated environment.

BRIEF DESCRIPTION OF THE DRAWINGS

The present invention should be more fully understood when the specification herein is taken in conjunction with the drawings appended hereto wherein.

DETAILED DESCRIPTION OF THE PRESENT INVENTION

A new drug, biological agent, therapeutic device or other potentially therapeutic substance or treatment must meet the approval of a government authority before it is marketed or commercially available to the public. In the United States, the Food and Drug Administration (FDA), has the authority to approve the use or sale of such products. The Federal Food, Drug and Cosmetic (FD&C) Act gives this authority to the FDA. "Drugs" are defined as "articles intended for use in the diagnosis, cure, mitigation, treatment or prevention of disease in man" and "articles (other than food) intended to affect the structure or any function of the body of man."

The general procedure for introducing a new drug or new FDA covered product in the United States begins with the creation or design of the product, e.g., a prosthesis, or the discovery or synthesis of the drug, or a determination that a previously-known drug may have a new therapeutic use. If the clinical safety of the product, or the chemical make-up of the product is not known on the basis of existing data, pre-clinical short-term animal studies may be undertaken to develop a pharmacological profile of the product and to determine the toxicity of it. When the reasonable safety of the product is established, the relevant data is then submitted to the FDA in an Investigational New Drug (IND) Application. The IND also includes a proposal for determining the safety and efficacy of the drug in clinical trials. The drug developer may then begin clinical trials if no objections are raised by the FDA upon review of the IND.

Clinical testing of a new product may involve numerous clinical studies and may take several years to complete. Such studies are ordinarily conducted in as many as three phases. Phase I clinical studies relate to basic safety investigations of the new drug in humans. A typical Phase I clinical study is conducted with a small number of healthy volunteer subjects to whom the drug is administered. The results obtained during Phase I studies are used to determine such parameters as the toxicity, absorption, metabolism, preferred route of administration and safe dosage range of the drug or other product. If the results from Phase I studies are favorable, the developer may proceed to Phase II studies.

In Phase II studies, the product is administered to controlled study group or groups of subjects having the problem for which the new product is believed to reduce or eliminate. Phase II studies are used to gather additional safety data and to provide initial results relating the effectiveness of the product (efficacy).

Prior to beginning Phase III studies, the drug or other product developer may provide data from completed or ongoing Phase I and Phase II studies to the FDA during periodic update reports or meetings. Phase III studies are undertaken in order to determine dosage, safety, and effectiveness in larger populations than the Phase II studies and to develop labeling and product insert information for the drug or other product.

At or near the conclusion of clinical testing, the developer is then ready to prepare a New Drug Application (NDA). An NDA is typically a massive document comprising several volumes of reports. Depending upon the type of drug, the NDA may include an index, a summary, and several sections relating to the chemistry, pharmacology, pharmacokinetics, clinical effects, and proposed labeling of the drug. Each one of these sections typically includes several documents involving thousands, tens of thousands or hundreds of thousands of pages. For example, the clinical section of an NDA may include an index, an abbreviated clinical summary, a risk/benefit analysis, an integrated summary of effectiveness, an integrated summary of safety data, clinical pharmacology study reports, controlled study reports, uncontrolled study reports, and other information pertaining to the accumulated knowledge and experience gained during clinical testing of the drug.

Each section of an NDA includes many cross-references among complex documents that relate to studies conducted over a period of time that can extend over several years. Thus, the composition of textual descriptions of study data, and the integration of such text into a consistent NDA can be a complex and time-consuming process. Once completed, the NDA is sent to the FDA for their review. The length of time required by the FDA to review an NDA is highly dependent upon the degree to which the NDA is well-organized, consistent, complete, and in compliance with the governing regulations and guidelines. Additionally, further documentation may be required in connection with clinical studies undertaken after submission of the NDA, or after approval of the drug. In other words, the FDA often seeks additional, supporting or primary source information before it renders a decision. The prescribed format and contents of an NDA are, of course, only suitable for obtaining review by the United States FDA. In order to obtain approval of the drug in other countries, essentially the same data may be required to be submitted to the respective governing authorities in each of the desired countries. For example, if it is also desired to market the new drug in Europe, then approval must be obtained from a corresponding administrative body of the European Union (EU). The EU has instituted a pre-marketing regulatory review program for new drugs that is similar to the NDA review program conducted by the FDA. Because the EU has formulated regulations for the review of new drugs that are in some ways different from the US regulations, the developer is burdened with the task of producing an additional set of hierarchically-related documents which rely upon the same data that was used to produce the NDA. Additionally, the developer may also desire to produce internal company reports which also present the same drug data in yet another customized format.

In the interest of reducing pre-marketing delay in the United States and abroad, the present invention has been developed to provide an automated system for managing all steps along the process usually conducted by a sponsor and/or a contractor, in real time, with actual original paperwork, computerized control, failsafe procedures, histories, text content, and many other steps, reports, details and summaries associated with drug studies, and for integrating such information in whatever forms that are ultimately necessary and desired by the company conducting the studies. Such a methodology is also useful for use in preparing documentation, such as Product License Applications or Establishment Licenses, in connection with studies relating to medical devices or to biological agents, such as viruses, sera, toxins, antitoxins, and the like.

Thus, it is a primary objective to reduce work required, reduce time required, increase quality control and quality assurance, eliminate changing or fixing documents and destroying or altering documents without a history record.

Another primary objective is to collect and capture many different types of documents, including the standard CRF documents described above, as well as regulating documents, rules, amendments, resumes, trip reports, emails, standard operating procedures.

It is also an object of the present invention to provide a system and software that would be adapted to arranging such information in the form of documents that are compliant with each of the various manners which may be prescribed for such documents by U.S. or foreign regulatory agencies, as well as those desired by the company developing the new product.

The following is a more detailed explanation of prior art conventional and present invention methodologies.

Chronology of Conventional Clinical Trial Data Collection (Prior Art)

Paper-based data collection is used for 95% of all clinical trials. A step by step description of clinical data collection follows:

1. A CRF book (case report form book) consisting of NCR tri-part paper divided up by patient visits is provided to investigator sites (where patients are examined) for each site, by the Sponsor (the product company, pharma or CRO—clinical research organization) running the trial.
2. a) At each site, patients are examined by the Principal Investigator, Sub-Investigators and/or Study Coordinators. Data is recorded in the patient's record file or on clinical note forms. This is commonly done by hand with clipboard and pen. The notes or other recorded information are permanently kept on site in the patient's record file. The pages where the data was first recorded are "source documents".
2. b) Alternatively, in a small number of cases, data is recorded in the patient's record file unless it's required on the CRFs and first recorded there. In these cases, the "source data" (e.g., where data is first recorded) is split between patient record files and the CRFs.

Note: "SOURCE" is a very key concept in clinical trial data collection. The common definition is that "source data" or "source documents" refers to where clinical data is first recorded—usually with paper and pen.

3. Source data is collected from patient record files, lab reports, hospital records, etc. regulatory documents and administrative forms and entered by hand onto the CRFs. This transcription usually is performed by a Study Coordinator who is looking at the "source" while transcribing.

Note: CRFs are pre-printed tri-part, NCR paper forms (yellow, white and pink copies) broken down into visits as prescribed by trial protocol and kept in three ring binders—one per patient.

CRF books with at least one copy of each page must stay on site and be available for audit purposes for years.

4. Monitors employed by the Sponsor/CRO come to the site to verify that the source was transcribed properly, to review records for accuracy and retrieve CRFs. This is done every four to six weeks. Once all source documents are verified against transcribed data and all data fields are checked for completeness and logic, the Monitor physically pulls two copies of each CRF page. These pages are mailed or carried to the Sponsor/CRO where they are collected and batched for key punching.

5. Keypunchers looking at the physical copies of the CRF pages, keypunch the data. Often this is performed as a double keypunch process in order to reduce transcription errors.

6. Clinical data is now in a computer database (could be spreadsheet or sophisticated database). Data is reviewed by Data Managers that review the data for completeness, errors, etc. At this time, edit checks (range checks) and logic test programs are run against the data. Questionable data is printed out and supplied to the Data Manager. The Data Manager must write up a "Data Query" for each instance of problem data and send the query to the appropriate Investigator or Study Coordinator.

7. Data Queries are received by Investigators/Study Coordinators and the "questions" are answered and sent back to the Data Manager. A Data Query can go back and forth many times before being resolved.

8. A complete audit trail of all data changes, data validation checks, conversations or e-mails between study coordinators and monitors, site visits by monitors and all data queries regarding all clinical data must be maintained. CRFs must be changed to match the final reconciled data values. A change in a CRF requires a date, who made the change, the new value and a note why the change was made. The word "reconciled" means that the source data value is visually verified as the same as the data value on the database. As an example of the magnitude of the task set forth above, in a large (3,000 patients) Phase III clinical trial lasting several years, there could be several hundred thousands of Data Queries involving over a hundred separate sites.

9. The above process is repeated for all CRF pages until a patient reaches the scheduled end of the study and the Principal Investigator signs the Final Report on that patient. \

Present Invention Methodology/Software

The present invention system software for improving the clinical trial process includes a primary design specification that supports the following: integrate and automate (1) document creation, capture, tracking and storage, (2) tracking clinical trial workflow activities and (3) tightly couple (reconcile and validate) clinical data, metadata (data about data) and administrative data with documents and workflow.

A second design specification of the present invention assures that data quality issues are best addressed as close as possible to the time and place of data creation. In other words, collecting, capturing and processing source documents and data at investigator sites as they are created is a necessary element of the present invention.

A third design specification of the present invention involves recording changes and modifications to documents and data with new versions of the document or data identified by a new version number, while retaining the original document or data. This process utilizes a system with software that includes preserving and documenting an audit trail of the history of each document, and in preferred embodiments, an audit trail of history for each separate data entry.

Thus, the present invention software and system is one that self validates and reconciles documents, work activity and data from the time of data/document capture until the locking of the clinical trial database after the completion of the trial.

The present invention software supports the following steps:

1. Providing a unique identifier for each data collection document. In a preferred embodiment, the system prints a pre-coded page. Such a page could be a Patient Consent Form, typical Case Report Form (CRF), an acknowledgement form or sign off form of various types or other data collecting document. (For example, the procurement of a signature is to be considered data collection.) Each document, and in preferred embodiments, each page, is uniquely bar coded. Information as to date, time, trial protocol, site, ID numbers may be included, and are preferably included, to uniquely identify each page.

2. Having all Investigator/Study Coordinators and other data collectors and data handlers, provide identification verification before being permitted to proceed.

3. Having appropriate documents (forms) for steps 1 above, where required.

4. Creating a permanent record of all signed filled out documents. In preferred embodiments, all system printed pages are scanned back into the software/computer system. The system will read (intelligent character recognition (ICR)) the unique bar code or other identifier and store the pages of the documents appropriately.

5. Independently, reviewing the originally filled in and signed documents to accept or require clarifications, and keeping a permanent record of the originally filled out and signed documents with no access for the Investigators/Study Coordinators to change or eliminate. In preferred embodiments, the system will permanently secure the documents for read only and hold in permanent storage. The system will attempt to ICR the handwritten fields or mark boxes of the scanned pages and create an e-page that will be a digital representation of the scanned page. Digital data will populate the various fields and edit check and predetermined logic test programs will be run against the digital data. Data will be compared to previously determined rules and, when conflicts are identified, will create alerts which become "workflow tasks" for the Investigators/Study Coordinators who is/are going to verify and otherwise "clean" the data. The process of storing, reviewing, creating new identifiers, returning to the Investigators/Study Coordinators is repeated (corrective iteration) until clean.

6. Having the Investigators/Study Coordinators (or other operators) obtain all relevant third party source (where clinical data were first recorded) documents—clinical notes, patient record form entries, lab results, etc. and follow the same procedures as set forth above. These documents are linked to the appropriate CFRs. In preferred embodiments, they will scan those documents into the system. One by one, these third party pages are linked, via a screen interface by the Study Coordinator to the corresponding CRFs.

7. Proving another level of further data cleaning, source validation, reconciliation, identifications and storage. In the preferred computerized system, data and documents are assembled as follows: (1) third party source documents, (2) the system printed, filled out in ink and scanned forms, (3) the virtual digital representation of the system printed, filled out, scanned originals and (4) a text file that records the various outcomes of related edit checks, logic tests and metadata (time, date, who, what, when, where) are assembled. The system generated interface walks a security cleared Investigator/Study Coordinator, Principal Investigator or other operator through each document, allowing ample opportunity (regulated procedures) to see that the ICR'd digital data is a true representation of the handwritten inked or other source document data. If non-ICR'd text data needs to be transcribed into the system or data are determined to be incorrect, the operator can transcribe text or change the data and state why the change was made. The system would track who, what, when and where. A change would create a new digital version of the page with a unique identifier and would be coded (color asterisk) that a change has been made. Edit checks and logic tests are run on the changed data.

8. Providing a document, and preferably a data-by-data point of entry history of all changes. In preferred embodiments, the system audit trail mechanism keeps track of all documents, data, edit checks, logic tests, data changes and the who, what, when, where, why of all workflow activity for each field of data that is "cleaned" (through the above processes).

9. Fully securing the audit trail as it is created so that it cannot ever be altered. This would be a read only audit trail.

10. Rendering the finished, clean, final version of each document as fully secured document. This would become a "locking" page or digital file, in preferred embodiments. When it's determined that the digital representation of each system printed page is verified and reconciled with source documents and is thus "cleaned", the digital representation page of the original system printed, filled out and scanned page is "locked" (never can be altered without nullifying the digital signature) with an operator's Private Key Digital Signature Sign Off (attests to the accuracy and authentication of the data and documents). As a result of the Sign Off action, the system similarly "locks" each related source document or text file containing edit check, logic tests, data changes and audit trail information.

In the present invention, in the software of the preferred embodiments, the terms "locks or locked" refer to the process of appending a Private Key generated Digital Signature to a page file in such a way that the related Public Key can read the file to determine if any change has been made to the file since it was first digitally signed. If there has been no change in the file, the Public Key will successfully "read" the Private Key Digital Signature—i.e. the "locked" page file. If a change occurred, then the Private Key Digital Signature could not be "read" as to that version of the document, and the file would be "not valid" and a true copy of the originally signed page file would have to be retrieved from the system (see explanation below).

All system documents or data are essentially data files that have a physical page-like appearance when displayed on a video monitor. It is critical that the video monitor page-like appearance be "locked" as a bit-mapped image (similar to a scanned image). This page-like image is what the operator sees when reconciling and verifying the original handwritten inked page and the digital representation of the original handwritten page. It is this bit mapped screen image of a page that is being signed by Private Key Digital Signature and is thus "locked". Signed Off bit mapped pages with common protocols can be viewed on many systems currently available, outside the scope and field of the present invention.

Thus, in this last step (10), self-validating files are created that, if authentic and valid, can be viewed anywhere and any time in the future using many operating systems supporting universal, generic page or file protocols.

Self validating is a necessary byproduct of successfully reading such files with the Public Key, and with the operator's Private Key Digital Signature. Reading a file's Private Key Digital Signature is accomplished by using the operator's known Public Key and applying special algorithms to the file. If the "reading" attempt results in a number that matches an encoded number attached to the file by the Private Key, then it's a mathematical certainty that the file has not changed from the instant that the Private Key Digital Signature was applied to the file. By this mechanism, any Private Key Digitally Signed file that can be "read" at any place and time on a network with a related Public Key must be 100% the same as it was when first signed. Such a file is said to be locked.

Thus, the preferred embodiment present invention described above permanently couples or relates (1) source documents, (2) system printed, filled out and scanned documents, (3) digital representation of the system printed filled out and scanned documents and (4) the related text pages that record the edit check, logic test, data change information and metadata. The relatedness of these files is originally maintained by the operator linking files together and the system labeling or bar coding on printed pages, the digital representation of those pages and the related text information files with header information or code identifiers. A single Private Key Digital Signature Sign Off session applies the digital signature to all related pages.

In some preferred embodiments of the present invention, the system process reconciles source data and documents with related work activities and digital data in the database at the point of time and place where a Study Coordinator or Principal Investigator or any operator commits documents or data to a clinical trial.

In addition to the above, various preferred embodiments of the present invention may include one or more of the following steps:

a. Other data changes can be made to data at later points in the process similar to the process outlined above. This process is called a "data query process" and is accomplished within the system applications. A complete versioning audit trail is maintained in the data query process where two or more participants question and reply to various document inaccuracies, inconsistencies or other problems.

b. Data files may initially be sent to a processing center, e.g. corporate headquarters or other company facility, or to a third party entity for authentication, validation, backup and disaster recovery purposes. Only data and documents passing Public Key "reading" authentication are accepted as trial data. Failed transmissions may require sites to sign off again on the related files and resend.

c. The Private/Public Key Digital Signature Sign Off and authentication process is performed every time a file is first transferred from a site to the Processing Center. However, subsequent file transfers or file access may or may not have to reverify digital signature authentication. The original Private/Public Key signed files are always available from the Processing Center to reverify that data in the database are the same as what was first recorded on source documents.

d. The term "work activity" as used throughout refers to activities of personnel working within the clinical trial process. Such process activities would typically be characterized by verbs as follows:

| Printed | Authored | Reviewed | Audited |
|---|---|---|---|
| Accessed | Certified | Replied | Signed |
| Viewed | Validated | Sent | Signed Off |
| Verified | Cleaned | Noted | Changed |
| Acknowledged | Monitored | Explained | Committed |
| Attested | Entered | Queried | Scanned |

Work activities could also be described as a series or group of implied tasks such as "site audit", "monitor site visit", "patient visit", etc. Work activity tracking by its very nature is metadata that gives "context" and "validity" to clinical data. For example, in preferred embodiments, the system records the time and date and who of a CRF page: printed time, filled out time, scanned time, cleaned time, transmitted to Process Center time, reviewed by monitor time and monitor signed off time create a logical timeline and audit trail. This would be a significant improvement over a paper-based system because a paper-based system would record only the visit time and maybe the keypunched time. The visit time might or might not correspond to the visit schedule, but the CRF could have been filled out three weeks after the visit and was back-dated—one cannot be certain with a paper-based system. In the present invention example given above, many computer clock times and many work activities have created a process timeline that cannot be accidentally or purposely altered.

e. The term workflow refers to the logical progression of steps that need to be taken according to the Trial Protocol, Good Clinical Practice (GCP) or administrative SOP. Examples: (1) a Patient Consent Form needs to be signed and countersigned and submitted to the system before the patient's first visit CRF is printed. (2) And if a Patient Consent Form is signed, then the system tells the Study Coordinator that a first patient visit must be scheduled. (3) Another example would be that the system prints a CRF and this event triggers the alert that the printed form must be scanned back into the system or be otherwise accounted for within x hours. (4) The approval of a new physician/investigator to the trial, triggers alerts requiring the collection of documents (license to practice in the state, curriculum vitae of Investigator), scheduling training classes in how to use the system or the critical aspects of the Protocol and the creation of new documents (revised 1572, signed contract and certification to use the system).

f. Source documents that have been scanned into the system at sites must be purged of patient identification for certain purposes—name, address, phone, SS#, etc. The bitmapped scanned image has to be obscured or removed where such identification information is displayed. In its place, the patient ID# and trial identification numbers would be stamped. These documents would be privacy protected in accordance with preset rules.

The purpose of this above process is to allow authenticated copies of source documents to be stored and accepted through the network without compromising the identity of a patient. Any trial related document held by a sponsor is subject to being copied and analyzed by the FDA. Any FDA trial document is accessible to the public through the Freedom of Information Act and, therefore, patient identification could become public knowledge. The FDA and Sponsors do not want the liability associated with releasing confidential patient information and this feature eliminates that concern.

Figure 1:
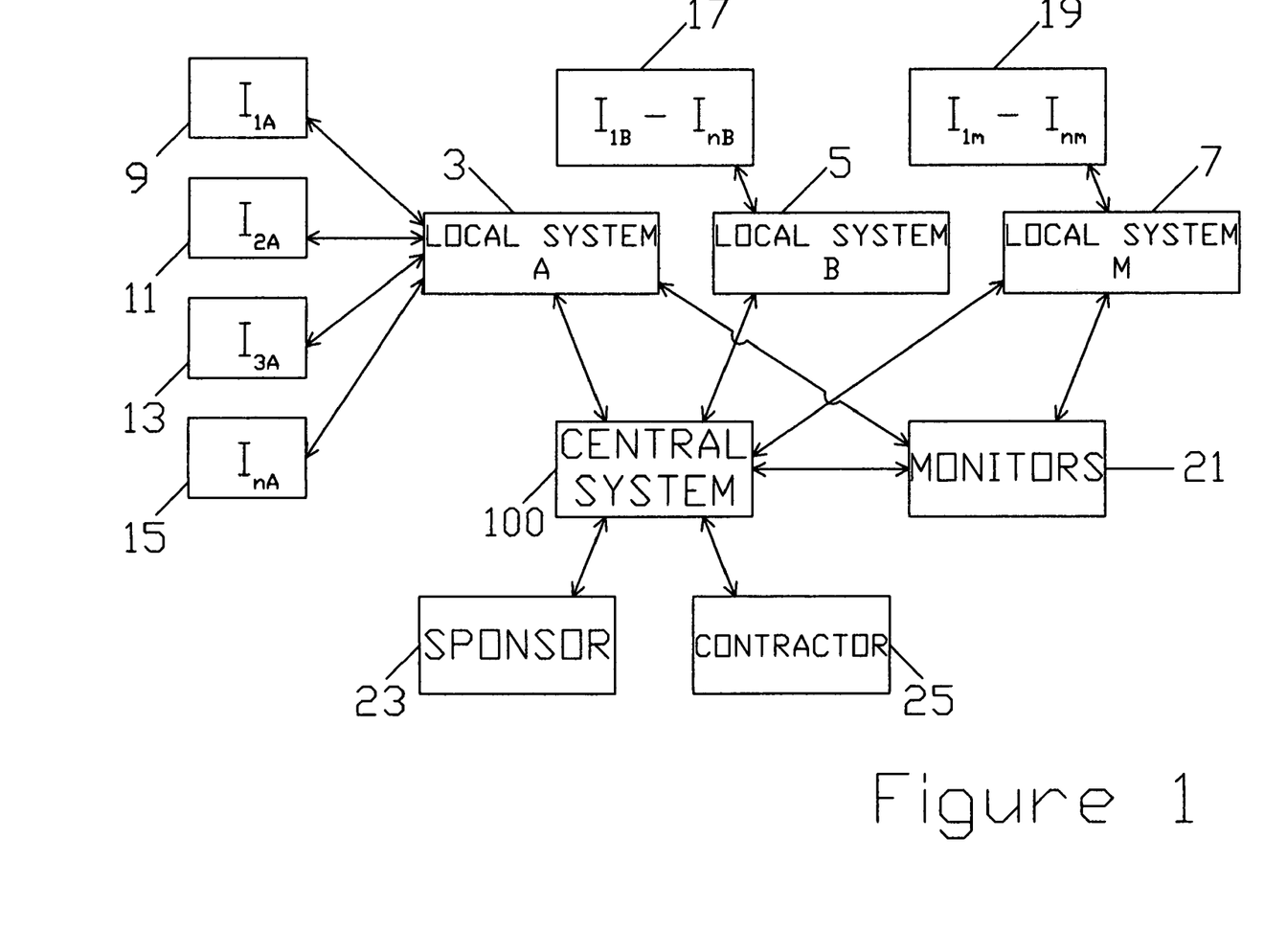
FIG. 1 shows a schematic flow diagram of the present invention system in its overall layout in one preferred embodiment, and in FIG. 2 shown a flow diagram of steps involved in present invention software.
Figure 2:
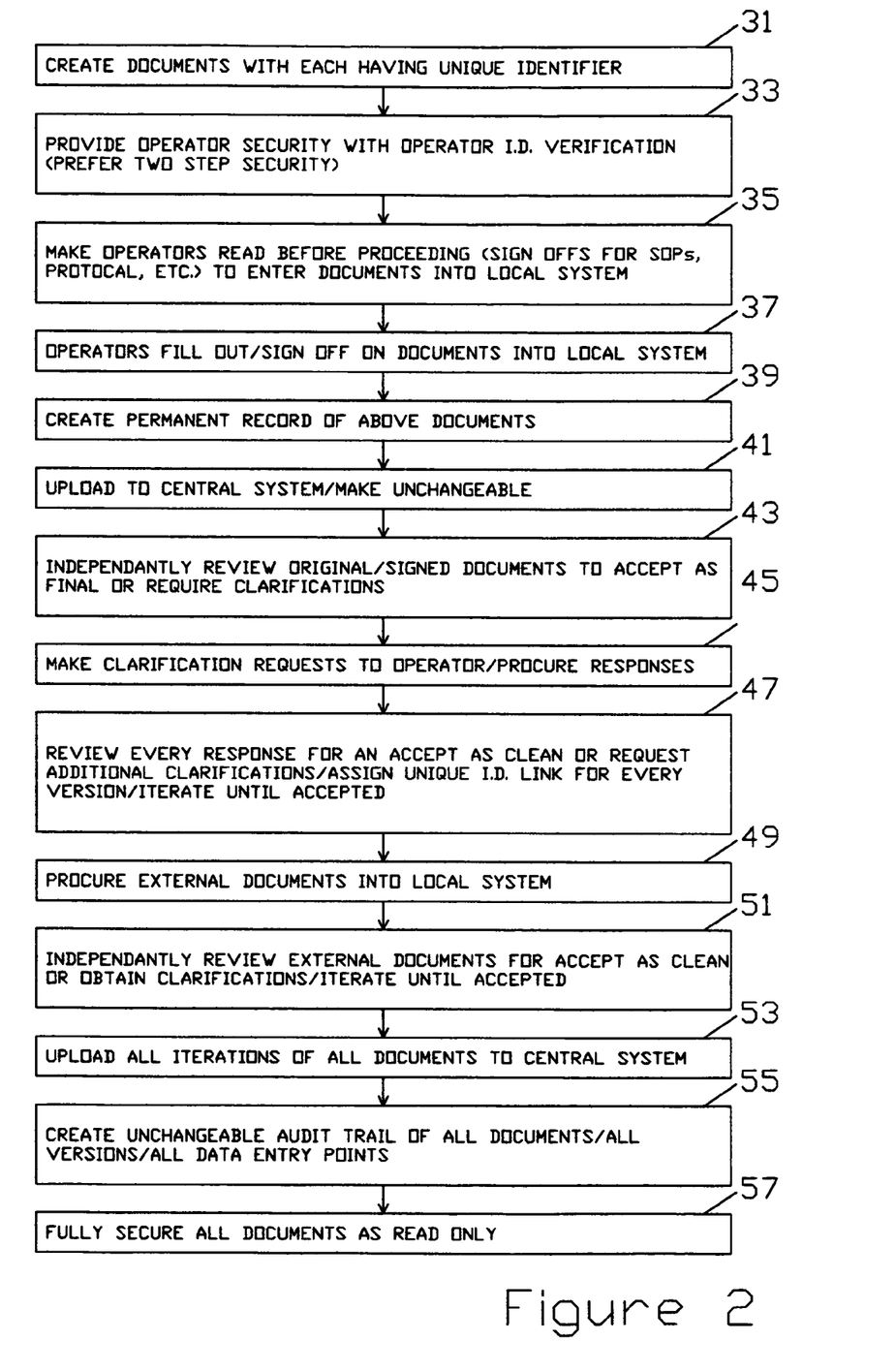

FIG. 1 shows a schematic flow diagram of the present invention in its overall layout in one preferred embodiment, and in FIG. 2 shown a flow diagram of steps involved in present invention. In FIG. 1, the present invention master system 1 is a setup with a central system 100 having at least one central computer connected to local system computers, and this central system 100 may be controlled in part by a sponsor 23 and in part by a contractor 25. There is a plurality of local systems with their own local computer(s) 3, 5, and 7, as well as monitors 21, who oversee and interact with the local systems and input and receive feedback from the central system. Each local system has a plurality of input operators such as operators 9, 11, 13 and 15 of local system 3. The other local systems 5 and 7 also have groups of input operators 17 and 19 respectively. The central system and local systems work together in accordance with the flow diagram shown in FIG. 2. Here, steps 31, 33, 35, 37, 39, 41, 43, 45, 47, 49, 51, 53, 55, and 57 are implemented to achieve to objectives of the present invention. These are generally performed sequentially, but are iteratively revisited for clarifications and monitoring queries. Also, the steps of procuring external documents may occur before or after some of the other steps and the order of sequence only becomes important relative to the proscribed sequences required by protocol and standard operating procedures.

Obviously, numerous modifications and variations of the present invention are possible in light of the above teachings. It is therefore understood that within the scope of the appended claims, the invention may be practiced otherwise than as specifically described herein.

What is claimed is:

1. A system for performing validated clinical studies of drug-type products, which comprises:

at least one computer-readable storage medium;

software stored on said at least one computer-readable storage medium, said software being sufficient software to support the following steps:

(a) creating a plurality of data collection documents that includes a plurality of diverse types of data collection documents and a plurality of each diverse type of data collection document, wherein every individual data collection document is provided its own unique identifier;

(b) providing a local system with operator security by having all operators and other data collectors and data handlers, complete identification verification before being permitted to proceed to add information into said local system utilizing said plurality of data collection documents;

(c) having appropriate operators who have successfully completed operator security fill out and sign specified data collection documents for step (a) above, where required;

(d) creating a permanent record of all filled out and signed data collection documents from step (c) and organizing and tracking said filled out and signed documents by their unique identifiers in said local system;

(e) providing a central system functionally connected to said local system, and uploading said permanent record to said central system;

(f) independently reviewing the originally filled out and signed data collection documents to accept said documents as clean or to require clarifications, and keeping a permanent record of all originally filled out and signed documents, with no access for the operators to change or eliminate data;

(g) as to said documents requiring clarifications, making clarification requests to the appropriate operator, and procuring response therefrom;

(h) independently reviewing each response in the form of a revised document, assigning a new unique identifier link to each version of every revised document and every subsequent version thereof, and repeating step (f) above iteratively until said documents are clean, and storing and tracking every version of every document in said central system;

(i) procuring relevant external clinical documents where data were first recorded, said external clinical documents being selected from the group consisting of clinical notes, patient record form entries, laboratory results, and combinations thereof, having the operators input said external clinical documents into said local system;

(j) providing another level of independent data cleaning, source validation, reconciliation, identifications and storage through a monitor query system of communications between monitors and operators that includes the same procedures as set forth in steps (f), (g) and (h) above;

(k) providing a document entry history to the local system and the central system of all changes to all documents within said central system to create an audit trail;

(l) fully securing the audit trail as it is created so that it cannot ever be altered; and, (m) rendering the finished, clean, final version of each document, as fully secured document that is a read-only document.

2. The system for performing validated clinical studies of drug-type products of claim 1 wherein said step (k) includes a data-by-data point of entry history to create an audit trail for every point of data entry having revisions.

3. The system for performing validated clinical studies of drug-type products of claim 1 wherein said step (b) includes a two part security clearance that includes at least two different types of security clearance, at least one of which is selected from the group consisting of password, voice recognition, signature recognition, retina recognition, fingerprint recognition, facial maps, and combinations thereof.

4. The system for performing validated clinical studies of drug-type products of claim 1 wherein said unique identifier includes a unique bar code that is an encrypted bar code containing a plurality of document related information, two of said plurality of document information selected from the group consisting of title of study, site of study, operator, patient name, patient identification number, date, document version, interviewer, monitor, query number, and combinations thereof.

5. The system for performing validated clinical studies of drug-type products of claim 1 wherein said audit trail is a drop down window that is click accessed at each point of data entry having a history of at least one revision.

6. The system for performing validated clinical studies of drug-type products of claim 1 wherein said filled out and signed data collection documents are read by intelligent character recognition (ICR) for handwritten inputs and converted to digital representations for storage and retrieval.

7. The system for performing validated clinical studies of drug-type products of claim 6 wherein, if an entry cannot be read by ICR, it will be treated as not clean and processed in accordance with steps (f), (g) and (h) above.

8. The system for performing validated clinical studies of drug-type products of claim 1 wherein said software includes the use of digital signature technology to fully secure said documents wherein said documents cannot be altered without nullifying an attached digital signature.

9. The system for performing validated clinical studies of drug-type products of claim 8 wherein said fully secured documents are locked by appending a private key generated digital signature thereto, and an operator's private key digital signature sign off creates said lock.

10. The system for performing validated clinical studies of drug-type products of claim 9 wherein said software also includes the steps of (n) presenting protocols and operating procedures to all local systems, and requiring all operators to review and sign off on some before being permitted to otherwise proceed on said local system.

11. A master system for performing validated clinical studies of drug-type products, which comprises:

A.) a central system connected to plurality of diversely located local systems, said central system including at least one host computer;

B.) a plurality of diversely located local system, each local system having at least one computer functionally connected to said central system at least one host computer; and, C.) sufficient software to support the following steps:

(a) creating a plurality of data collection documents that includes a plurality of diverse types of data collection documents and a plurality of each diverse type of data collection document, wherein every individual data collection document is provided its own unique identifier;

(b) providing a local system with operator security by having all operators and other data collectors and data handlers, complete identification verification before being permitted to proceed to add information into said local system utilizing said plurality of data collection documents;

(c) having appropriate operators who have successfully completed operator security fill out and sign specified data collection documents for step (a) above, where required;

(d) creating a permanent record of all filled out and signed data collection documents from step (c) and organizing and tracking said filled out and signed documents by their unique identifiers in said local system;

(e) providing a central system functionally connected to said local system, and uploading said permanent record to said central system;

(f) independently reviewing the originally filled out and signed data collection documents to accept said documents as clean or to require clarifications, and keeping a permanent record of all originally filled out and signed documents, with no access for the operators to change or eliminate data;

(g) as to said documents requiring clarifications, making clarification requests to the appropriate operator, and procuring response therefrom;

(h) independently reviewing each response in the form of a revised document, assigning a new unique identifier link to each version of every revised document and every subsequent version thereof, and repeating step (f) above iteratively until said documents are clean, and storing and tracking every version of every document in said central system;

(i) procuring relevant external clinical documents where data were first recorded, said external clinical documents being selected from the group consisting of clinical notes, patient record form entries, laboratory results, and combinations thereof, having the operators input said external clinical documents into said local system;

(j) providing another level of independent data cleaning, source validation, reconciliation, identifications and storage through a monitor query system of communications between monitors and operators that includes the same procedures as set forth in steps (f), (g) and (h) above;

(k) providing a document entry history to the local system and the central system of all changes to all documents within said central system to create an audit trail;

(l) fully securing the audit trail as it is created so that it cannot ever be altered; and, (m) rendering the finished, clean, final version of each document, as fully secured document that is a read-only document.

12. The master system of claim 11 wherein said step (k) includes a data-by-data point of entry history to create an audit trail for every point of data entry having revisions.

13. The master system of claim 11 wherein said step (b) includes a two part security clearance that includes at least two different types of security clearance, at least one of which is selected from the group consisting of password, voice recognition, signature recognition, retina recognition, fingerprint recognition, facial maps, and combinations thereof.

14. The master system of claim 11 wherein said unique identifier includes a unique bar code that is an encrypted bar code containing a plurality of document related information, two of said plurality of document information selected from the group consisting of title of study, site of study, operator, patient name, patient identification number, date, document version, interviewer, monitor, query number, and combinations thereof.

15. The master system of claim 11 wherein said audit trail is a drop down window that is click accessed at each point of data entry having a history of at least one revision.

16. The master system of claim 11 wherein said filled out and signed data collection documents are read by intelligent character recognition (ICR) for handwritten inputs and converted to digital representations for storage and retrieval.

17. The master system of claim 16 wherein, if an entry cannot be read by ICR, it will be treated as not clean and processed in accordance with steps (f), (g) and (h) above.

18. The master system of claim 11 wherein said software includes the use of digital signature technology to fully secure said documents wherein said documents cannot be altered without nullifying an attached digital signature.

19. The master system of claim 18 wherein said fully secured documents are locked by appending a private key generated digital signature thereto, and an operator's private key digital signature sign off creates said lock.

20. The master system of claim 19 wherein said software also includes the steps of (n) presenting protocols and operating procedures to all local systems, and requiring all operators to review and sign off on some before being permitted to otherwise proceed on said local system.

* * * * *